US006423860B1

United States Patent
Lewis et al.

(10) Patent No.: US 6,423,860 B1
(45) Date of Patent: Jul. 23, 2002

(54) METHOD FOR PROMOTING DIALKYLDIHALOSILANE FORMATION DURING DIRECT METHOD ALKYLHALOSILANE PRODUCTION

(75) Inventors: Larry Neil Lewis, Scotia; William Jessup Ward, Niskayuna; David Cheney DeMoulpied, Athens; John Matthew Bablin, Amsterdam; Martha Maples Gardner, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/655,423

(22) Filed: Sep. 5, 2000

(51) Int. Cl.⁷ .................................................. C07F 7/16
(52) U.S. Cl. ...................................................... 556/472
(58) Field of Search .......................................... 556/472

(56) References Cited

U.S. PATENT DOCUMENTS

| 4,500,724 A | 2/1985 | Ward et al. |
| 4,602,101 A | 7/1986 | Halm et al. |
| 4,762,940 A | 8/1988 | Halm et al. |
| 4,898,960 A | 2/1990 | Dosaj et al. |
| 4,946,978 A | 8/1990 | Halm et al. |
| 5,059,343 A | 10/1991 | Halm et al. |
| 5,059,706 A | 10/1991 | Degen et al. |
| 5,596,119 A | 1/1997 | Halm et al. |
| 5,654,460 A * | 8/1997 | Rong ......................... 556/472 |
| 5,777,146 A * | 7/1998 | Straussberger et al. ..... 556/472 |
| 5,847,181 A * | 12/1998 | Nakanishi et al. .......... 556/472 |
| 5,874,604 A * | 2/1999 | Steiner et al. .............. 556/472 |
| 6,057,469 A * | 5/2000 | Margaria et al. ............ 556/472 |

FOREIGN PATENT DOCUMENTS

WO            9501303            1/1995

OTHER PUBLICATIONS

"The Control of the Methylchlorosilane Product Disribution From the Rochow Direct Process", C.S. Kuivila, R.H. Zapp, L.K. Wilding and C.A. Hall, Silicon for the Chemical Industry III, Sandefjord, Norway, Jun. 18–20, 1996, pp. 227–238.

* cited by examiner

*Primary Examiner*—Paul F. Shaver
(74) *Attorney, Agent, or Firm*—Bernadette M. Bennett; Noreen C. Johnson

(57) ABSTRACT

Dialkyldihalosilane formation during direct method alkylhalosilane production is promoted by effecting reaction between alkyl halide and powdered silicon in the presence of a catalyst comprising copper, zinc, and aluminum and further comprising an amount of phosphorus and tin wherein the amount of phosphorus and tin substantially enhances the selectivity of dialkyldihalosilane formation in comparison to the selectivity of dialkyldihalosilane formation in the presence of the catalyst comprising copper, zinc, aluminum and tin without phosphorus.

21 Claims, 2 Drawing Sheets

METHOD FOR PROMOTING DIALKYLDIHALOSILANE FORMATION DURING DIRECT METHOD ALKYLHALOSILANE PRODUCTION

BACKGROUND OF THE INVENTION

The present invention is directed to a method for enhancing the formation and recovery of dialkyldihalosilane from alkylhalosilane crude. More particularly, the present invention relates to a direct method for methylchlorosilane manufacture by maintaining an optimum amount of tin and phosphorus in the catalyst.

Prior to the present invention, methylchlorosilanes, hereinafter sometimes designated "methylchlorosilane" for brevity, were made by effecting a reaction between powdered silicon and methyl chloride in the presence of a copper-zinc-tin catalyst, as shown by U.S. Pat. No. 4,500,724, Ward et al., assigned to the same assignee as the present invention. Silicon (Si) is typically combined with copper (Cu) in a range between about 0.5% and about 10% by weight copper relative to silicon, zinc (Zn) in a range between about 0.01 part and about 0.5 part per part copper, and tin (Sn) in a range between about 200 parts per million and about 3,000 parts per million per part of copper.

By the prior art method, there is produced a mixture of alkylhalosilanes and in particular, methylchlorosilanes. As utilized hereinafter, the term "methylchlorosilanes" includes dimethyldichlorosilane (Di), which is the preferred methylchlorosilane, and a variety of other silanes such as tetramethylsilane, trimethylchlorosilane (Mono), methyltrichlorosilane (Tri), silicon tetrachloride, trichlorosilane, methyldichlorosilane (MH), and dimethylchlorosilane ($M_2H$).

In addition to the above methylchlorosilanes, residue is also formed during the production of methylchlorosilane crude. "Crude" as used herein refers to the unpurified product mixture of methylchlorosilanes. "Residue" as used herein refers to products in the methylchlorosilane crude that have a boiling point greater than about 70° C. at atmospheric pressure. Residue typically consists of such materials as disilanes, for example, symmetrical 1,1,2,2-tetrachlorodimethyldisilane, 1,1,2trichlorotrimethyldisilane, disiloxanes, disilmethylenes, and other higher boiling species, for example, trisilanes, trisiloxanes, and trisilmethylenes.

Generally, it is desirable to effect high rates of production in the methylchlorosilane reaction as well as selectively produce dimethyldichlorosilane over the other products. New techniques are constantly being sought to improve the selectivity of the methylchlorosilane reaction as well as increase the yield of the methylchlorosilane products.

SUMMARY OF THE INVENTION

The present invention provides a method for promoting the formation of dialkyldihalosilane during direct method alkylhalosilane production, the method comprising effecting reaction between alkyl halide and powdered silicon in the presence of a catalyst comprising copper, zinc, and aluminum and further comprising an amount of phosphorus and tin wherein the amount of phosphorus and tin substantially enhances the selectivity of dialkyldihalosilane formation in comparison to the selectivity of dialkyldihalosilane formation in the presence of the catalyst comprising copper, zinc, aluminum and tin without phosphorus.

DETAILED DESCRIPTION OF THE INVENTION

Figure 1:
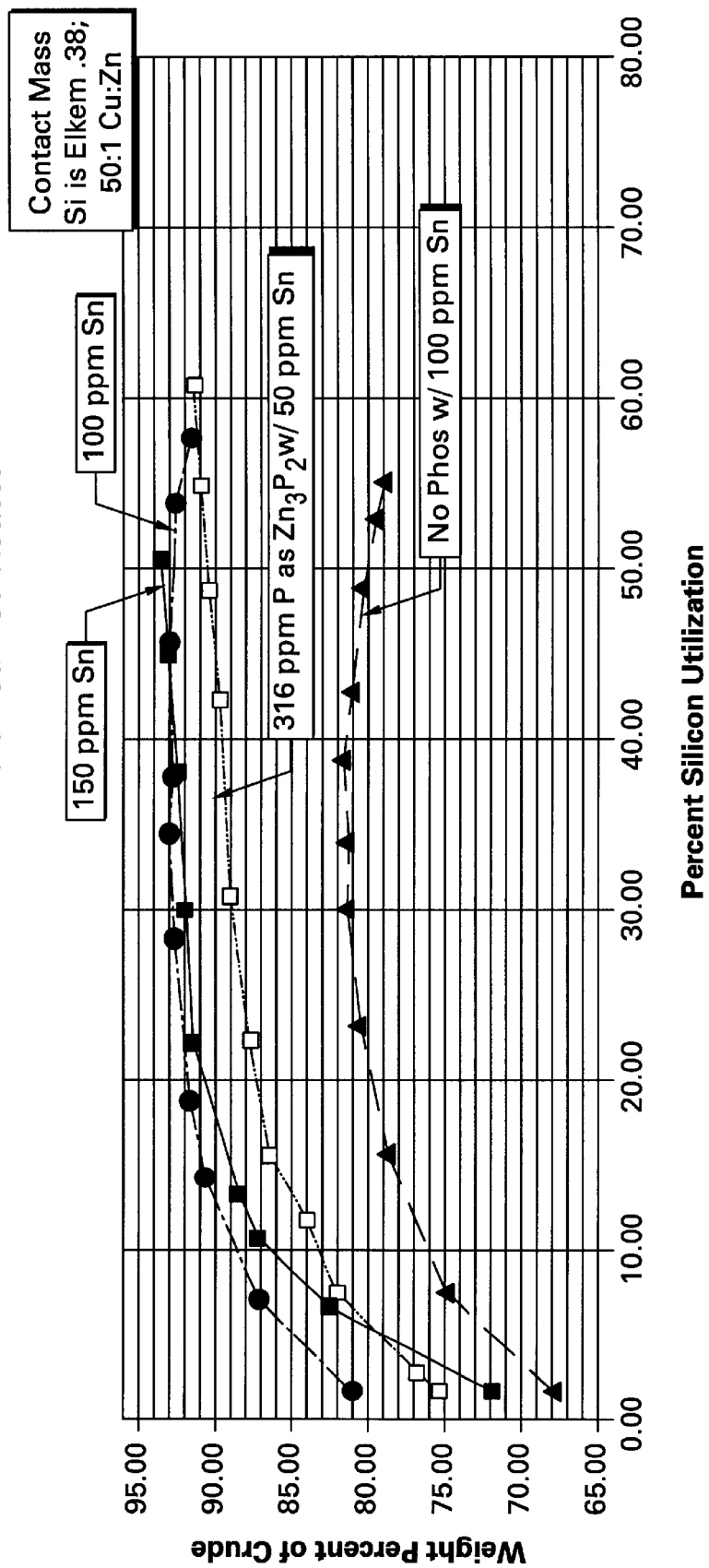
FIG. 1 shows weight percent of dimethyldichlorosilane produced at varying levels of tin with and without phosphorus.

The present invention relates to a process involving the reaction of methyl chloride and silicon in the presence of a direct method catalyst containing optimal amounts of tin and phosphorus. "Direct method" as used herein refers to the process of passing an alkyl halide through a bed of copper and silicon to yield alkylhalosilanes. "Direct method catalyst" as used herein refers to a combination of constituents which increase the rate of reaction and selectivity to dialkyldihalosilanes. Constituents of the direct method catalyst typically include tin, zinc, copper, phosphorus, aluminum, and combinations thereof. While tin is recognized as a constituent of direct method catalyst, its effectiveness for dialkyldihalosilane formation during direct method operation can be substantially enhanced by introducing phosphorus into the reactor while maintaining a high tin content. "Substantially enhanced" dialkyldihalosilane formation as used herein refers to an increase in the amount of dialkyldihalosilanes produced in comparison to the amount of dialkyldihalosilanes produced with a catalyst containing copper, zinc, aluminum and tin without phosphorus. Typically, the dialkyldihalosilane formation is substantially enhanced when the percentage of dialkyldihalosilanes produced is greater than about 80% based on total alkylhalosilanes produced. The presence of phosphorus and tin has a synergistic effect on the process for making dialkyldihalosilanes. Phosphorus is present in a range between greater than about 100 parts per million (ppm) and less than about 1000 ppm based on the weight of the total reaction mixture and preferably, in a range between greater than about 100 ppm and about 500 ppm based on the weight of the total reaction mixture. Tin is present in a range between about 10 ppm and about 150 ppm based on the weight of the total reaction mixture and preferably, in a range between about 15 ppm and about 30 ppm based on the weight of the total reaction mixture. "Total reaction mixture" as used herein refers to the weight of the combination of silicon and catalyst. If the tin level is too low or too high, it has been unexpectedly found that the addition of phosphorus does not have an effect on the amount of the dialkyldihalosilane produced. In addition, the small scale laboratory reactors typically require an amount of tin in a range between about 2 and about 3 times greater than the level used for large scale commercial reactors to achieve the effect on the amount of dialkyldihalosilane produced in a reactor used for production purposes.

Copper and zinc are present in the direct method catalyst. Copper is typically present in a range between about 1% by weight and about 10% by weight copper relative to silicon, and preferably in a range between about 3% by weight and about 5% by weight. Zinc is typically present in a range between about 400 ppm and about 2000 ppm per part copper, preferably in a range between about 400 ppm and about 700 ppm per part copper. Aluminum is also present in a range between about 500 ppm and about 5000 ppm per part copper, and preferably in a range between about 1000 ppm and about 2500 ppm per part copper.

The tin used in the present invention can come from a variety of sources. "Source" as used herein refers to the chemical compound which provides the necessary element or elements for the direct reaction catalyst. Sources of tin include, but are not limited to, tin metal dust, tin halides, tin oxide, tetramethyl tin, alkyl tin halides, brass, bronze, and combinations thereof.

The sources of phosphorus that may be used include, but are not limited to, copper phosphide ($Cu_3P$), zinc phosphide ($Zn_3P_2$), phosphorus trichloride ($PCl_3$), alkylphosphines ($R_3P$) such as triethylphosphine [$(C_2H_5)_3P$] and trimethylphosphine [$(CH_3)_3P$], and combinations thereof.

Among the copper compounds that can be used as copper sources in the practice of the present invention are carboxylate salts of copper, partially oxidized copper, and combinations thereof. Additional copper sources include, but are not limited to, particulated cupric chloride and cuprous chloride, copper flake, brass, bronze, and combinations thereof.

Examples of effective sources of zinc include, but are not limited to, zinc metal powder; halides of zinc, such as zinc chloride; zinc oxide; and combinations thereof.

The aluminum used in the direct reaction catalyst is supplied from various sources. The source of aluminum, for instance, may comprise aluminum powder, various alloys including, but not limited to, copper-aluminum alloy, silver-aluminum alloy, silicon-aluminum alloy, magnesium-aluminum alloy, and combinations thereof.

Although methyl chloride is the alkyl halide of choice for the alkylhalosilane reaction, other alkyl halides such as $C_{1-4}$ alkyl chlorides, for example, ethyl chloride, propyl chloride, etc., also can be used. Correspondingly, the term "alkylhalosilane" includes dialkyldihalosilanes such as dimethyldichlorosilane (Di), which is the preferred alkylhalosilane, and a variety of other alkylhalosilanes such as trimethylchlorosilane (Mono), methyltrichlorosilane (Tri), silicon tetrachloride, trichlorosilane, methyldichlorosilane (MH), and dimethylchlorosilane ($M_2H$), and also tetramethylsilane.

Among the processes which can be used in the practice of the present invention, there are included those in which at least one reactor comprises a fixed bed, a stirred bed, or a fluid bed. The present invention can be practiced in a continuous, semi-continuous, or batch manner. More specifically, a fixed bed reactor may be a column that contains silicon particles through which alkyl halide gas passes. A stirred bed may be similar to a fixed bed in which there is mechanical agitation of some sort in order to keep the bed in constant motion. Reaction typically occurs at a temperature in a range between about 250° C. and about 350° C., and preferably in a range between about 280° C. and about 320° C. It is also advisable to carry out the reaction under a pressure in a range between about 1 atmosphere and about 10 atmospheres in instances where a fluid bed reactor is used since higher pressure increases the rate of conversion of methyl chloride to methylchlorosilanes. Desirably, the pressure is in a range between about 1.1 atmospheres and about 3.5 atmospheres and preferably in a range between about 1.3 atmospheres and about 2.5 atmospheres.

The expression "semi-continuous conditions" with respect to the description of processes means that reactants are added and the reactor is run until about 50% of the silicon has been utilized. After about 50% silicon utilization, additional silicon and catalysts may be added. With a batch mode reaction, all of the reactant components are combined and reacted until most of the reactants are consumed. In order to proceed, the reaction has to be stopped and additional reactants added. A fixed bed and stirred bed may both be run under batch conditions. A fluidized reactor is typically run under continuous conditions. With continuous conditions, the reaction does not have to be stopped in order to add more reactants.

In instances where a fluid bed reactor is used, methyl chloride, an inert gas such as argon, or mixture thereof can be used to fluidize the bed of silicon particles. The silicon particles can have a mean diameter below about 700 microns, with an average size of greater than about 20 microns and less than about 300 microns being preferred. Preferably, the mean diameter of the silicon particles is in a range between about 100 microns and about 150 microns. Silicon used in the alkylhalosilane reaction can have an iron (Fe) content in a range between about 0.1% and about 1% by weight based on total silicon, calcium (Ca) content in a range between about 0.01% and about 0.2% by weight based on total silicon, and an aluminum (Al) content in a range between about 0.02% and about 0.5% by weight based on total silicon. Silicon is usually obtained at a purity of at least about 98% by weight of silicon and it is then comminuted to particles of powdered silicon for preparation of the contact mass. "Contact mass" as used herein refers to a source of copper which is pre-reacted with a silicon powder. The contact mass is typically prepared by reacting silicon and a copper source such as cuprous chloride at a temperature in a range between about 280° C. and about 400° C. in a furnace in an inert atmosphere like nitrogen or argon until evolution of silicon tetrachloride ($SiCl_4$) ceases. The contact mass may be added to the reactor with other catalyst components. "Pre-contact mass" as used herein refers to a mixture of cuprous chloride, silicon, and tin which is not reacted.

Analysis of the alkylhalosilane product may be conducted to determine crude composition. Silicon utilization is determined by weighing crude samples of the alkylhalosilane product at various times. Typically data is recorded at about 20% by weight silicon utilization. Selectivity may be determined by gas chromatography, "GC", with thermal conductivity detectors. Individual silane component analysis is performed by comparision to reagent grade silanes. GC calibrations are performed by analysis of silane mixtures of known composition. Percent dimethyldichlorosilane produced is of particular interest in the present invention.

In addition to percent dimethyldichlorosilane produced, another measure of performance of the methylchlorosilane reaction is the rate of crude methylchlorosilane formation. The reaction rate constant for methylchlorosilane formation is based on the rate of methylchlorosilane production and is measured as grams of crude silane per grams of silicon per hour. The amount of tin and phosphorus in the present invention enhances the rate of methylchlorosilane formation as well as decreases the amount of residue formed.

Those skilled in the art are also interested in the T/D weight ratio of the methylchlorosilane crude. The T/D ratio is the ratio of the methyltrichlorosilane (T or Tri) to dimethyldichlorosilane (D or Di) in the crude methylchlorosilane reaction product. Accordingly, an increase in the T/D ratio indicates that there is a decrease in the production of the preferred dimethyldichlorosilane. When tin and phosphorus are added to the direct method reaction and the tin content exceeds about 150 parts per million, the T/D ratio generally increases.

In order that those skilled in the art will be better able to practice the present invention, the following examples are given by way of illustration, and not by way of limitation. All parts are by weight unless otherwise indicated.

General Procedure

The fluid bed reactor was a 3.8 centimeter (cm) inside diameter (ID) glass tube with a glass frit at the center to support the silicon bed. The reactor was heated by a second concentric 5.1 cm ID glass tube coated with tin oxide to which two pairs of electrodes were attached to create two heated sections.

In order to fluidize the silicon it was necessary both to stir the reacting silicon and to vibrate the reactor. Pulverized silicon was used. The silicon was produced by Elkem Chemicals and was taken from a standard lot made for plant feed. A large quantity of this silicon was ground and the resulting ground powder was used as feed to the lab reactors. The surface area was 0.38 meters$^2$/gram. The elemental composition of the silicon was as follows (ppm):

| Al | Ca | Fe | P |
|---|---|---|---|
| 1800 | 20 | 5000 | 40 |

Vibration was accomplished by attaching one end of a clamp to the reactor, and the other end to the base of a variable intensity test tube shaker. By adjusting the intensity of the vibration and the firmness with which the clamp gripped the reactor, the necessary agitation of the silicon bed was achieved. Typically vibration was used intermittently during a run.

A typical contact mass was prepared as follows: silicon (40 grams, 0.38 micron mean diameter) was combined with hexane (5.43 grams) and a 25% solids hexane slurry (12.67 grams) composed of copper chloride and 48 ppm tin dust for a copper to tin ratio of 1000:1. The mixture was taken to dryness first by evaporation under a stream of nitrogen and then by heating in a vacuum oven at 100° C. At this point the mixture could be used as a pre-contact mass of copper chloride, silicon, and tin. A true contact mass was used for this example. To make a true contact mass the dried solid of copper chloride, silicon, and tin was place in a crucible and then into a furnace under a flow of argon and then heated to 350° C. until silicon tetrachloride evolution ceased (ammonium hydroxide indicator used to monitor composition of effluent). In this example, 3.12 g of copper chloride should produce 7.9 mmol of silicon tetrachloride or a theoretical weight loss of 1.34 g. The actual weight loss in this case was 1.41 g.

The reaction of approximately 20 grams of contact mass was performed at 300° C. or 310° C. as measured by a thermocouple immersed in the contact mass. The reactor was fed methyl chloride in a range between about 93 standard cubic centimeters per minute (sccm) and about 97 sccm. Product silanes were collected across a condenser system maintained at −20° C.

The reactor and downstream glassware heating and cooling systems were brought to their set temperatures and the reactor was first purged with argon (30 minutes at 95 sccm) and then methyl chloride (1 hour at 95 sccm). After purging, the contact mass was charged into the reactor through a funnel. Following the addition of the contact mass, the reactor stirring and vibration was begun. Condensate samples of 1 to 2 grams were collected on an hourly basis.

EXAMPLE 1

The following methylchlorosilane reaction was carried out in a fluid bed reactor in accordance with the General Procedure. The fluid bed reactor was charged with silicon composed of pre-reacted contact mass 5% by weight copper chloride based on the original weight of copper chloride (contact mass) and 1000 ppm zinc dust [20 milligrams (mg) per 20 gram (g)], all amounts based on the weight of the total composition charged to the reactor. The amount of tin (as tin dust) was varied in a range between about 50 ppm and about 150 ppm. The reactor was then heated to 310° C. under a methyl chloride flow. Crude product, methylchlorosilane crude, was collected manually and weighed to determine reaction rate and then analyzed by Gas Chromatography. Rate, % dimethyldichlorosilane (as a percent of total crude product), % methyldichlorosilane and T/D ratio were compared at the 20% silicon utilization point.

In the following cases, 500 ppm phosphorus was added to the reactor in the form of copper phosphide and in one case it was added as zinc phosphide (316 ppm phosphorus). It was not surprising that an increase of tin from 50 ppm to 150 ppm gave an increase in residue. However, it was unexpectedly found that when tin was increased from 50 ppm to 150 ppm and phosphorus was added, an increased selectivity for dimethyldichlorosilane occurred at the expense of methyltrichlorosilane and residue. These results are shown in FIG. 1 for dimethyldichlorosilane and FIG. 2 for residue.

The graph in FIG. 1 shows the impact phosphorus has, at a 500 ppm level, on promoting dimethydichlorosilane formation during direct method methylchlorosilane production. As shown by the graph, tin levels in a range between about 50 ppm and about 150 ppm were particularly effective for increasing the efficiency of the process of making dimethyldichlorosilanes in the presence of phosphorus.

Figure 2:
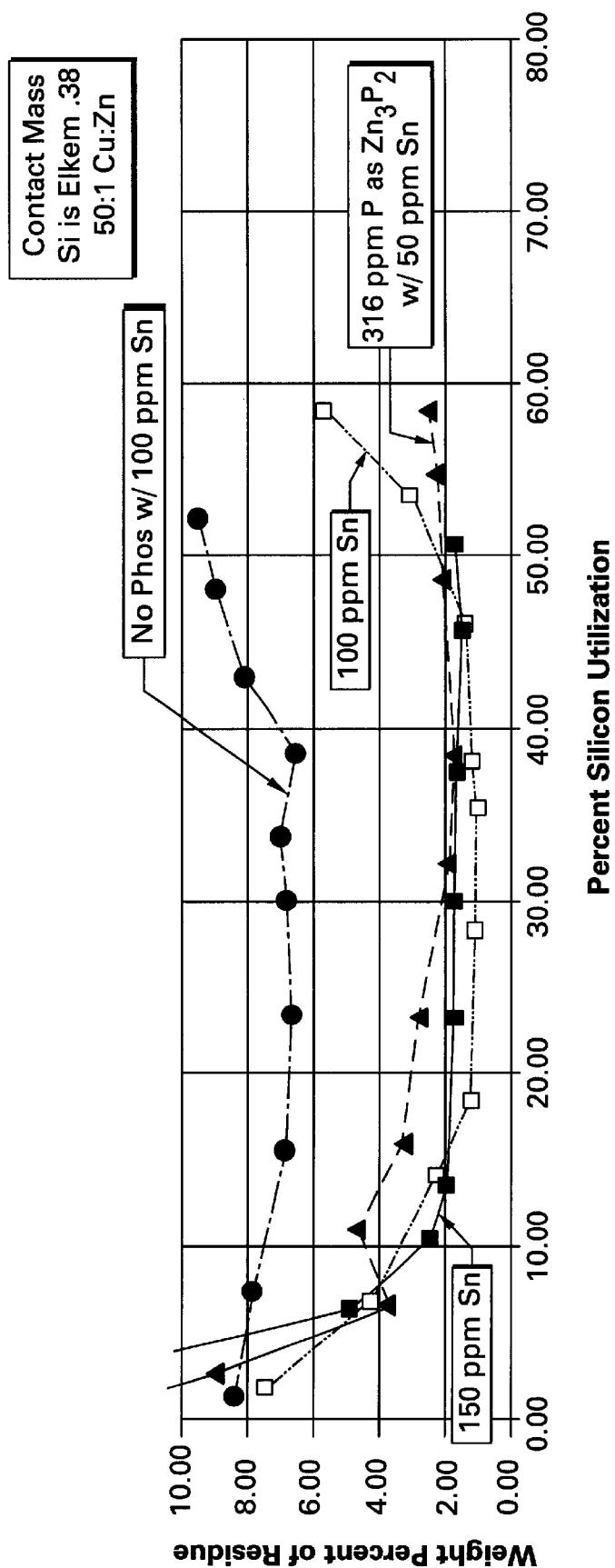
FIG. 2 shows weight percent of residue produced at varying levels of tin with and without phosphorus.

The graph in FIG. 2 shows the impact phosphorus has, at a 500 ppm level, on decreasing the amount of residue formed during direct method methylchlorosilane production. As shown by the graph, tin levels in a range between about 50 ppm and about 150 ppm were particularly effective for decreasing the amount of residue formed in the process of making dimethyldichlorosilanes in the presence of phosphorus.

EXAMPLE 2

The following two methylchlorosilane reactions were carried out in a fluid bed reactor in accordance with Example 1 at a temperature of 310° C. The fluid bed reactor was charged with silicon composed of 5% copper chloride (precontact mass) and either 5000 ppm zinc dust (100 mg per 20 g) or 1500 ppm zinc dust (30 mg per 20 g), all amounts based on the weight of the total composition charged to the reactor. Both experiments were initially reacted in the absence of tin. During the course of the experiments, amounts of tin (as tin dust) were added, varying in a range between about 25 ppm and about 50 ppm. Consistent with both experiments was the result of the methylchlorosilane reaction without tin, as shown in Table 1. It was not surprising that methylchlorosilane reactivity increased with the addition of tin from 0 ppm to 25 ppm. However, it was unexpectedly found that when additional tin was added to the reaction, methylchlorosilane reactivity ceased to increase.

TABLE 1

Effect of Bed [Sn] on Cumulative Crude Selectivity

| Run # | Bed [Sn] ppm | % Di | T/D | Residue (%) | Normal Rate (g/g-silicon-hr) | [Zn] |
|---|---|---|---|---|---|---|
| 1 | 0 | 69.1 | .132 | 6.70 | .02 | 5000 |
| 1 | 25 | 86.7 | .072 | 2.86 | .08 | 5000 |
| 1 | 50 | 85.4 | .082 | 2.74 | .23 | 5000 |
| 1 | 100 | 80.5 | .103 | 7.33 | .23 | 5000 |
| 2 | 0 | 63.6 | .158 | 7.30 | .03 | 1500 |

TABLE 1-continued

Effect of Bed [Sn] on Cumulative Crude Selectivity

| Run # | Bed [Sn] ppm | % Di | T/D | Residue (%) | Normal Rate (g/g-silicon-hr) | [Zn] |
|---|---|---|---|---|---|---|
| 2 | 25 | 86.5 | .077 | 2.73 | .11 | 1500 |
| 2 | 75 | 85.4 | .086 | 2.66 | .04 | 1500 |

EXAMPLE 3

The following two methylchlorosilane reactions were carried out in a fluid bed reactor in accordance with Example 1 at a temperature of 310° C. The fluid bed reactor was charged with silicon composed of 5% copper chloride (pre-contact mass), 5000 ppm zinc dust, and 50 ppm tin dust. Both experiments were reacted to a similar silicon utilization point prior to the addition of 5 mg of tin as tin dust (Sn) or tin tetrachloride ($SnCl_4$). Consistent with both experiments was the result of the methylchlorosilane reaction after the tin addition. It was unexpectedly found that when the additional tin was added to the reaction, 250 ppm by weight of the combination of silicon and catalyst, the comparative methylchlorosilane reactivity declined and the amount of residue increased.

TABLE 2

Effect of Bed [Sn] on Cumulative Crude Selectivity and Rate

| Run # | [Sn] ppm | Amount of Silicon Utilized (%) | Di | T/D | Residue % | Normal Rate (g/g-silicon-hr) |
|---|---|---|---|---|---|---|
| 1 | 50 | 28 | 82.7 | .115 | 4.1 | .39 |
| 1 | 300 | 15 | 72.3 | .183 | 10.4 | .06 |
| 2 | 50 | 19 | 80.0 | .131 | 4.7 | .30 |
| 2 | 300 | 21 | 71.5 | .193 | 10.5 | .09 |

EXAMPLE 4

The following methylchlorosilane reaction was carried out in a fluid bed reactor in accordance with Example 1 at a temperature of 310° C. The fluid bed reactor was charged with silicon composed of 5% weight based on the original weight of copper chloride (contact mass), and 75 ppm tin dust. The equivalent of 3350 ppm zinc was added as $ZnCl_2$ (Zinc chloride—99.99% Aldrich) to the reaction followed by an addition of 3100 ppm phosphorus as trimethylphosphine (1.0 molar $P(CH_3)_3$ in toluene Aldrich). A significant improvement in selectivity followed the phosphorus addition; however the reacting bed mass exhibited visual agglomeration. This agglomeration or "bed stickiness" would preclude the use of high levels of phosphorus as demonstrated here.

EXAMPLE 5

The following methylchlorosilane reaction was carried out in a fixed bed reactor. A fixed bed reactor was set up consisting of a 20 cm long by 1.3 cm diameter outside diameter (OD) glass tube with a glass frit located 6 cm from the end to support the bed. Since the silicon was not stirred and the methylchlorosilane reaction is highly exothermic, the diameter of the bed was limited by heat transfer considerations. The thermal conductivity of the silicon was assumed to be the same as sand, namely 0.2 BTU/ft-hr-° F. The highest anticipated reaction rate was 1 gram of crude silane/gram of silicon-hour. For this rate, a temperature rise of about 10° C. along the center line of the reactor was calculated. Over this temperature range, no changes in crude composition were observed. The other reactor design consideration was pressure drop. To be practical and safe, a pressure drop of no more than approximately 5 pounds per square inch (psi) was considered acceptable, and this limited the bed size to 6 grams.

The reactor was centered vertically in a 5 cm glass tube wrapped with Nichrome® ribbon or coated with tin oxide. Two pairs of electrodes were fitted to the tin oxide or Nichrome to create two heated sections. One section was for the inlet to the system, and was used to preheat the methyl chloride feed. The other section was for the reactor itself. The 5 cm heated glass tube was centered in a 6.4 cm glass tube used for insulation of the reactor and for safety.

The reactor was charged with 6 g of solid (pre-contact mass) composed of silicon with CuCl (2.5% by weight), elemental zinc (2.8 mg) and elemental tin (0.15 mg). The reaction was run under a flow of methyl chloride, 35 sccm at 315° C. At 20% silicon utilization, the crude product contained 89.7% dimethyldichlorosilane. The experiment was repeated except that 100 ppm phosphorus in the form of triethylphosphine was added. At 20% silicon utilization, the crude product was composed of 88.5% dimethyldichlorosilane indicating that this low level of phosphorus did not lead to improved selectivity. This example defines the lower effective limit of phosphorus as being greater than about 100 ppm phosphorus.

EXAMPLE 6

The methylchlorosilane reaction was carried out as described in Example 5 with a 500 ppm phosphorus level. At 20% silicon utilization, the crude product was composed of 93.9% dimethyldichlorosilane indicating a strong promoting effect at this level of phosphorus.

EXAMPLE 7

The methylchlorosilane reaction was carried out as described in Example 5 except that 1000 ppm phosphorus was used. At 20% silicon utilization, the crude was composed of 91% dimethyldichlorosilane indicating that phosphorus was still a strong promoter at this level. However, the reactor bed was sticky with 1000 ppm phosphorus. Due to the problems with stickiness under these conditions, an effective maximum useful amount of phosphorus is less than about 1000 ppm.

While typical embodiments have been set forth for the purpose of illustration, the foregoing descriptions should not be deemed to be a limitation on the scope of the present invention. Accordingly, various modifications, adaptations, and alternatives may occur to one skilled in the art without departing from the spirit and scope of the present invention.

What is claimed is:

1. A method for promoting the formation of dialkyldihalosilane during direct method alkylhalosilane production, the method comprising effecting reaction between alkyl halide and powdered silicon in the presence of a catalyst comprising copper, zinc, and aluminum and further comprising an amount of phosphorus and tin wherein the phosphorus is present in a range between greater than about 100 parts per million and less than about 1000 parts per million based on the weight of the combination of silicon and catalyst;

tin is present in a range between about 10 parts per million and about 150 parts per million based on the weight of the combination of silicon and catalyst; and wherein the amount of phosphorus and tin substantially enhances the selectivity of dialkyldihalosilane formation in comparison to the selectivity of dialkyldihalosilane formation in the presence of the catalyst comprising copper, zinc, aluminum and tin without phosphorus.

2. The method in accordance with claim 1, where the phosphorus is in a range between greater than about 100 parts per million and about 500 parts per million based on the weight of the combination of silicon and catalyst.

3. The method in accordance with claim 2 where the tin is in a range between about 15 parts per million and about 30 parts per million based on the weight of the combination of silicon and catalyst.

4. The method in accordance with claim 1, where the reaction is conducted in a fixed bed reactor.

5. The method in accordance with claim 1, where the reaction is conducted in a stirred bed reactor.

6. The method in accordance with claim 1, where the reaction is conducted in a continuous manner.

7. The method in accordance with claim 1, where the reaction is conducted in a fluid bed reactor.

8. The method in accordance with claim 1, where the zinc is present in a range between about 400 parts per million and about 2000 part per million per part copper.

9. The method in accordance with claim 8, where the zinc is present in a range between about 400 parts per million and about 700 parts per million copper.

10. The method in accordance with claim 1, where the aluminum is present in a range between about 500 parts per million and about 4000 parts per million per part copper.

11. The method in accordance with claim 10, where the aluminum is present in a range between about 1000 parts per million and about 2500 parts per million copper.

12. The method in accordance with claim 1, where the copper is present in a range between about 1% and about 10% by weight copper relative to silicon.

13. The method in accordance with claim 12, where the copper is present in a range between about 3% and about 5% by weight copper relative to silicon.

14. The method in accordance with claim 1, where the phosphorus is introduced into the reactor as copper phosphide, an alkylphosphine, phosphorus trichloride, or combinations thereof.

15. The method in accordance with claim 14, where the phosphorus is introduced into the reactor as triethylphosphine.

16. The method in accordance with claim 14, where the phosphorus is introduced into the reactor as trimethylphosphine.

17. The method in accordance with claim 1, where the alkyl halide comprises methyl chloride.

18. A method for promoting the formation of dimethyldichlorosilane in a continuous manner during direct method methylchlorosilane production, the method comprising:

effecting reaction in a fluid bed reactor between methyl chloride and powdered silicon in the presence of a catalyst comprising copper, aluminum, zinc, tin, and phosphorus having an average proportion of copper in a range between about 3% and about 5% based on the weight of silicon;

tin in a range between about 15 parts per million and about 30 parts per million based on the weight of the combination of silicon and catalyst; and phosphorus in a range between greater than about 100 parts per million and about 500 parts per million, based on the weight of the combination of silicon and catalyst.

19. The method in accordance with claim 18, where the phosphorus is introduced as copper phosphide.

20. The method in accordance with claim 18, where the phosphorus is introduced as phosphorus trichloride.

21. The method in accordance with claim 18, where the phosphorus is introduced as triethylphosphine.

* * * * *